United States Patent
Cordero et al.

(10) Patent No.: US 10,548,939 B1
(45) Date of Patent: Feb. 4, 2020

(54) OAT AND MARIGOLD BASED COMPOSITION WITH ANTI-INFLAMMATORY AND WOUND HEALING ACTION AND METHOD OF PREPARING SAME

(71) Applicant: Dr. Cordero Pediatric Office, Inc., Naples, FL (US)

(72) Inventors: Hector Cordero, Naples, FL (US); Alejandrina Carmenaty-Bozza, Naples, FL (US)

(73) Assignee: Dr. Cordero Pediatrics Office, Inc., Naples, FL (US)

( * ) Notice: Subject to any disclaimer, the term of this patent is extended or adjusted under 35 U.S.C. 154(b) by 0 days.

(21) Appl. No.: 16/100,886

(22) Filed: Aug. 10, 2018

(51) Int. Cl.
| | | |
|---|---|---|
| *A61K 36/00* | (2006.01) |
| *A61K 36/899* | (2006.01) |
| *A61K 36/28* | (2006.01) |
| *A61K 31/665* | (2006.01) |
| *A61K 33/30* | (2006.01) |
| *A61K 31/355* | (2006.01) |
| *A61P 17/02* | (2006.01) |
| *A61K 47/14* | (2017.01) |
| *A61K 47/10* | (2017.01) |
| *A61K 9/06* | (2006.01) |
| *A61K 9/107* | (2006.01) |
| *A61K 9/00* | (2006.01) |
| *A61K 47/36* | (2006.01) |

(52) U.S. Cl.
CPC .......... *A61K 36/899* (2013.01); *A61K 9/0014* (2013.01); *A61K 9/06* (2013.01); *A61K 9/107* (2013.01); *A61K 31/355* (2013.01); *A61K 31/665* (2013.01); *A61K 33/30* (2013.01); *A61K 36/28* (2013.01); *A61K 47/10* (2013.01); *A61K 47/14* (2013.01); *A61K 47/36* (2013.01); *A61P 17/02* (2018.01)

(58) Field of Classification Search
None
See application file for complete search history.

(56) References Cited

U.S. PATENT DOCUMENTS

2017/0216368 A1* 8/2017 Moreno Gonzalez ................... A61K 36/28

* cited by examiner

*Primary Examiner* — Qiuwen Mi
(74) *Attorney, Agent, or Firm* — Mark Terry

(57) ABSTRACT

A lotion for topical application for treating skin conditions, comprising of: about 25.0 to 80.0 percent by weight of deionized water, about 1.0 to 12.0 percent by weight of caprylic/capric triglyceride, about 0.5 to 10.0 percent by weight of cetyl alcohol, about 0.5 to 6.0 percent by weight of glycerin, about 0.5 to 10.0 percent by weight of cetearyl olivate and sorbitan olivate, about 0.5 to 2.0 percent by weight of *Avena sativa* kernel flour, about 0.05 to 2.0 percent by weight of sodium ascorbyl phosphate, about 0.10 to 5.0 percent by weight of zinc PCA, about 0.05 to 5.0 percent by weight of tocopheryl acetate, about 0.05 to 5.0 percent by weight of *Calendula officinalis* flower extract, about 0.10 to 5.0 percent by weight of xantham gum, and at least 0.05 percent by weight of a preservative mixture solution.

1 Claim, 12 Drawing Sheets

PRIOR ART

OAT AND MARIGOLD BASED COMPOSITION WITH ANTI-INFLAMMATORY AND WOUND HEALING ACTION AND METHOD OF PREPARING SAME

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

The claimed embodiments relate generally to compositions for treating skin conditions, and more specifically, to compositions that promote the healing of wounds and alleviate pain and inflammation at a site.

BACKGROUND

Skin conditions or skin disorders include a variety of different afflictions, including eczema, burns, rashes, irritations, decubitus ulcers, diabetes induced skin lesions where there is inflammation, skin cell disruption, dead cells and secondary skin infection due to the presence of inflammatory cells and inflammatory substances. Skin conditions or skin disorders can also vary greatly in symptoms and severity. Skin conditions can be temporary or permanent and may be painless or painful. Some skin conditions have situational causes, such as the presence of an inflammatory substance, while others may be genetic, such as eczema. Some skin conditions can be minor, such as first-degree burns, while others can be life-threatening, such as a staph infection in the dermis. The aforementioned skin conditions can lead to poor tissue perfusion, improper delivery of nutrients to the damaged cells, lack of nutrients for the formation of collagen, improper melanocyte growth and poor delivery of anti-inflammatory substances to the damaged tissue.

A common treatment for said skin conditions include the use of anti-inflammatory painkillers, which can be consumed orally in the form of tablets, liquids or capsules, injected via needle, or applied to skin in the form of a topical gel or cream. The mechanisms of action for said anti-inflammatories is varied. When applied to skin in the form of a topical preparation, the anti-inflammatory painkillers may be referred to as topical non-steroidal anti-inflammatory drugs (NSAIDs) or just topical anti-inflammatories as a generic term.

But while topical steroids have important benefit in reducing inflammation, they also have significant side effects. Side effects consist of: 1) skin atrophy, which causes thinning of the epidermis and changes in the connective tissue of the dermis, wrinkled skin, hypopigmentation and prominence of underlying veins, 2) alteration in immune function, which can inhibit the skin's ability to fight off bacterial or fungal infections, 3) tachyphylaxis, i.e., the tolerance the skin develops to the vaso-constrictive action of topical steroids, 4) steroid rosacea, comprising redness and pustules commonly observed in fair skinned people, 5) topical steroid allergy, 6) stretch marks in areas where skin touches skin such as the groin and armpits, most of which are itchy, permanent and irreversible, 7) immune-suppression, which is caused when topical steroids are used to treat skin infections of fungal origin, causing the user to get a rash that gets redder, itchier and spreads more extensively than a typical fungal infection. For these reasons, the use of topical steroidal creams should be used with caution.

Therefore, a need exists to overcome the problems with the prior art as discussed above, and particularly for a more efficient way of providing wound healing and anti-inflammatory compositions for treating skin conditions while reducing side effects.

SUMMARY

This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

The disclosed embodiments are directed to a formulation, where the anti-inflammatory and wound healing activities of oat and marigold are within a precise proportion of a lotion to obtain an effective wound healing and anti-inflammatory topical preparation. The lotion may relieve inflammatory conditions of various origins and promote wound healing at the localized area.

The lotion for topical application for treating skin conditions, comprises: about 25.0 to 80.0 percent by weight of deionized water, about 1.0 to 12.0 percent by weight of caprylic/capric triglyceride, about 0.5 to 10.0 percent by weight of cetyl alcohol, about 0.5 to 6.0 percent by weight of glycerin, about 0.5 to 10.0 percent by weight of cetearyl olivate and sorbitan olivate, about 0.5 to 2.0 percent by weight of *Avena sativa* kernel flour, about 0.05 to 2.0 percent by weight of sodium ascorbyl phosphate, about 0.10 to 5.0 percent by weight of zinc PCA, about 0.05 to 5.0 percent by weight of tocopheryl acetate, about 0.05 to 5.0 percent by weight of *Calendula officinalis* flower extract, about 0.10 to 5.0 percent by weight of xantham gum, and at least 0.05 percent by weight of a preservative mixture solution.

In another embodiment, a method of preparation of said lotion is disclosed. The method includes the steps of: adding the following ingredients to a first vessel and heating to about 80 degrees Celsius: about 25.0 to 80.0 grams of deionized water, about 0.5 to 6.0 grams of glycerin, about 0.5 to 2.0 grams of *Avena sativa* kernel flour, about 0.10 to 5.0 grams of zinc PCA, and about 0.10 to 5.0 grams of xantham gum, adding the following ingredients to a second vessel and heating to about 80 degrees Celsius: about 1.0 to 12.0 grams of caprylic/capric triglyceride, about 0.5 to 10.0 grams of cetyl alcohol, about 0.5 to 10.0 grams of cetearyl olivate and sorbitan olivate, and about 0.05 to 5.0 grams of *Calendula officinalis* flower extract, adding the ingredients of the first vessel to the ingredients in the second vessel and mixing until creating a mixture, mixing the mixture in the second vessel until homogenized, allowing the mixture to cool to about 40 degrees Celsius, adding the following ingredients to the mixture in the second vessel: about 25.0 to 80.0 grams of deionized water, about 0.05 to 2.0 grams of sodium ascorbyl phosphate, and about 0.05 to 5.0 grams of tocopheryl acetate, mixing the mixture until homogenized, mixing the mixture for a period of time, adding the following ingredient to the mixture in the second vessel: at least 0.05 grams of a preservative mixture solution, and, allowing the mixture in the second vessel to cool to about 25 to 30 degrees Celsius.

The lotion for topical application for treating skin conditions, comprises: about 0.5 to 2.0 percent by weight of *Avena sativa* kernel flour, about 0.05 to 2.0 percent by weight of sodium ascorbyl phosphate, about 0.10 to 5.0 percent by weight of zinc PCA, about 0.05 to 5.0 percent by weight of tocopheryl acetate, and about 0.05 to 5.0 percent by weight of *Calendula officinalis* flower extract.

To the accomplishment of the above and related objects, claimed subject matter may be embodied in the form illustrated in the accompanying drawings, attention being called to the fact, however, that the drawings are illustrative only, and that changes may be made in the specific construction illustrated and described within the scope of the appended claims. The foregoing and other features and advantages of the claimed embodiments will be apparent from the following more particular description of the preferred embodiments, as illustrated in the accompanying drawings.

BRIEF DESCRIPTION OF THE DRAWINGS

The accompanying drawings, which are incorporated in and constitute part of this specification, illustrate embodiments of the claimed subject matter and together with the description, serve to explain the principles of the disclosed embodiments. The embodiments illustrated herein are presently preferred, it being understood, however, that the claimed subject matter is not limited to the precise arrangements and instrumentalities shown, wherein:

DETAILED DESCRIPTION

Figure 1:
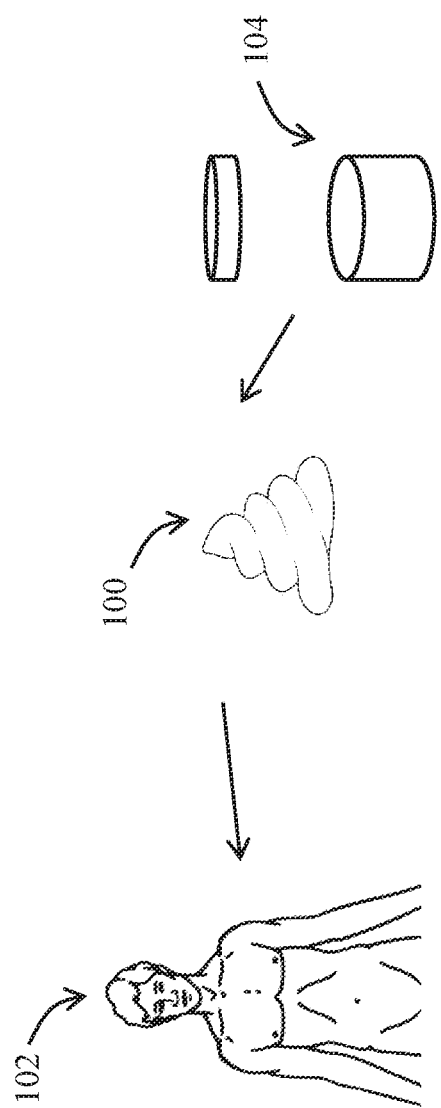
FIG. 1 is a view of an embodiment of the oat and marigold-based composition with anti-inflammatory and wound healing action depicting its use.

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions or modifications may be made to the elements illustrated in the drawings, and the methods described herein may be modified by substituting, reordering, or adding additional stages or components to the disclosed methods and devices. Accordingly, the following detailed description does not limit the disclosed embodiments. Instead, the proper scope of the disclosed embodiments is defined by the appended claims.

The disclosed embodiments include a lotion that comprises *Avena sativa* (oat), marigold, zinc PCA, tocopherol acetate and sodium ascorbyl phosphate, among other things, that exerts anti-inflammatory and wound healing properties when applied to skin, acts rapidly, can be used while wearing clothes, does not spoil easily, and is simple to apply. The preservatives added protect the formulation from microbial activity or growth.

The disclosed embodiments include a formulation, where the anti-inflammatory and wound healing effects of *Avena sativa* (oat), marigold, zinc PCA, tocopherol acetate and sodium ascorbyl phosphate are enhanced within an appropriate matrix to obtain an effective wound healing and anti-inflammatory topical preparation that can be effectively and easily applied to the skin condition. The disclosed embodiments may ease inflammation, itching, burning, and irritation, while also promoting healing of wounds, burns, scratches, abrasions, sores, broken skin, infections and the like. The disclosed embodiments can be applied at the localized site, thus preventing the harshness of orally consumed NSAIDs, which may have adverse effects on gastrointestinal tracts of the user due to active ingredients such as ibuprofen, diclofenac, felbinac, ketoprofen, or piroxicam that may cause digestive issues.

The disclosed embodiments combine active ingredients *Avena sativa* (oat), marigold, zinc PCA, tocopherol acetate and sodium ascorbyl phosphate in an oil and water lotion emulsion. The disclosed embodiments are used in treating eczema, burns, early stages of decubit ulcers, diabetes induced skin lesions where there is inflammation, skin cell disruption, dead cells, and possibly secondary skin infection due to the presence of inflammatory cells and inflammatory substances. The disclosed embodiments have a desirable aesthetic look and feel, while also exhibiting ease of application, and a uniform product that is stable.

Unlike other unstable products that separate into two or more phases or strata during its shelf life or at completion of packaging the product, the disclosed embodiments are homogenized and remain stable during their shelf life. Whereas other products may have precipitated particulate matter or ingredients that have been improperly incorporated, the disclosed embodiments are made uniform and smooth for an aesthetic look and feel. The disclosed embodiments effectively deliver the combined actives and the method of manufacture is designed to maintain the integrity of the active ingredients during the manufacturing process. The disclosed embodiments are also designed to deliver the combined of actives in a uniform fashion on the skin with ease of application, which includes ease of spreading the product on the skin with uniform coverage. The aesthetic feel of the product is smooth and uniform and has a desirable feel during product dispensing, during application, and after the completed application.

FIG. 1 is a view of the disclosed embodiments depicting the use of the *Avena sativa* (oat), marigold, zinc PCA, tocopherol acetate and sodium ascorbyl phosphate-based composition with anti-inflammatory and wound healing action. FIG. 1 shows that the composition 100 (or formulation), which may be a lotion, gel, emulsion or cream, may be stored and distributed in a container 104. Subsequently, the composition 100 may be removed from the container 104 and applied to the afflicted site of the skin on the patient 102. The composition 100 is structured to be applied topically to the skin in small amounts to cure the patient's affliction, such as inflammation of the skin. A small amount is defined as an amount of lotion that easily fits on the finger or hand of the applying individual. A regimen may be used with the composition 100, such as applying the composition 100 to the patient's skin periodically, such as once a day, every morning, for a defined period of time, such as for two weeks.

As used herein the following terms are intended to have meaning as follows: namely, anti-inflammatory composition, composition, and formulation meaning pharmaceutical compositions formulated and compounded with a topical substance matrix, such as a lotion or gel. A gel or gel matrix means a colloid that is almost fully liquid which is immobilized by surface tension between it and macromolecular network of fibers built from a small amount of a substance gelating material present.

The lotion or composition 100 for topical application for treating skin conditions, comprises: about 25.0 to 80.0 percent by weight of deionized water, about 1.0 to 12.0 percent by weight of caprylic/capric triglyceride, about 0.5 to 10.0 percent by weight of cetyl alcohol, about 0.5 to 6.0 percent by weight of glycerin, about 0.5 to 10.0 percent by weight of cetearyl olivate and sorbitan olivate, about 0.5 to 2.0 percent by weight of *Avena sativa* kernel flour, about 0.05 to 2.0 percent by weight of sodium ascorbyl phosphate, about 0.10 to 5.0 percent by weight of zinc PCA, about 0.05 to 5.0 percent by weight of tocopheryl acetate, about 0.05 to 5.0 percent by weight of *Calendula officinalis* flower extract, about 0.10 to 5.0 percent by weight of xantham gum, and at least 0.05 percent by weight of a preservative mixture solution.

Deionized water, or demineralized, is water that has had all or almost all of its mineral ions removed, such as cations like sodium, calcium, iron, and copper, and anions such as chloride and sulfate. Deionized water prevents the clarity and viscosity from being negatively affected due to carbopol polymers' sensitivity to hard water ions.

Figure 2:
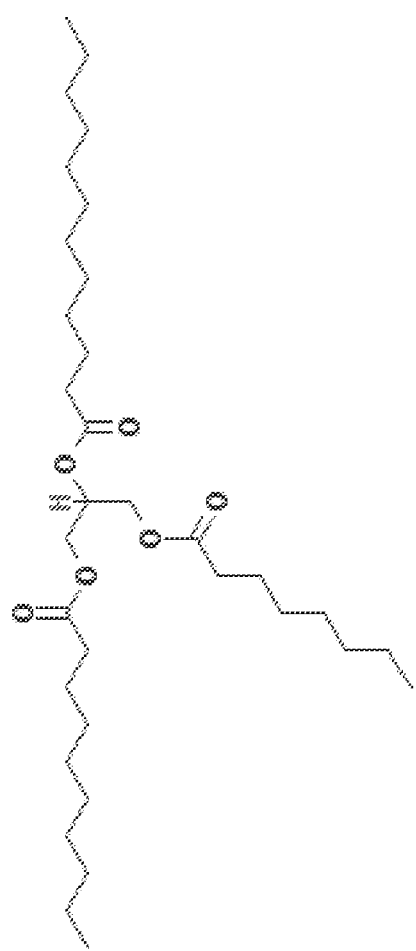
FIG. 2 is a perspective view of the molecular structure of caprylic/capric triglyceride.

Caprylic/capric triglyceride is a mixed triester derived from coconut oil and glycerin. It comes in the form of an oily liquid and is sometimes mistakenly referred to as fractionated coconut oil. Caprylic/capric triglyceride mainly works as an emollient, dispersing agent and solvent. Caprylic/capric triglyceride is included in many cosmetics due to its mix of fatty acids that skin can use to replenish its surface and resist moisture loss. The molecular structure of caprylic/capric triglyceride is represented by the structure 200 shown in FIG. 2.

Figure 3:
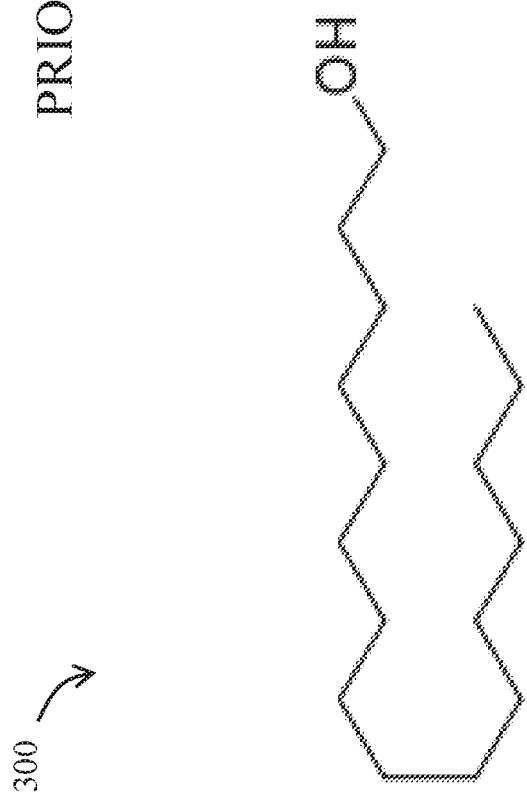
FIG. 3 is a perspective view of the molecular structure of cetyl alcohol.

Cetyl alcohol is a fatty alcohol with the formula $CH_3(CH_2)_{15}OH$. At room temperature, cetyl alcohol takes the form of a waxy white solid or flakes. Cetyl alcohol is used in the cosmetic industry as an opacifier in shampoos, or as an emollient, emulsifier or thickening agent in the manufacture of skin creams and lotions. It is also employed as a lubricant. The molecular structure of cetyl alcohol is represented by the structure 300 shown in FIG. 3.

Figure 5:
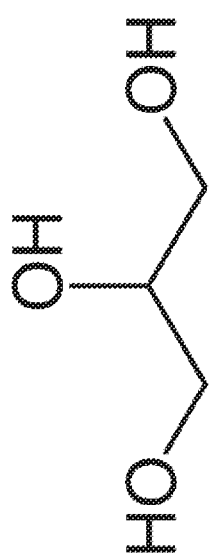
FIG. 5 is a perspective view of the molecular structure of glycerin.

Glycerin meaning gliceryn, glycerol, glycerine, 1,2,3-propanetriol, glyceritol, glycyl alcohol, trihydroxypropane, propanetriol, osmoglyn, and 1,2,3-trihydroxypropane is a trihydroxy sugar alcohol with three hydroxyl groups that are responsible for its solubility in water and its hygroscopic nature and may function in the composition as humectant, improving smoothness, providing lubrication, emollient agent, skin conditioning agent, skin protector, and viscosity decreasing agent as represented by the molecular structure 500 shown in FIG. 5.

Glycerin is widely used as humectantin cosmetics and personal care products, also as hair conditioning agent, in skin creams and lotions, in shaving preparations, deodorants, make up, oral care agent, skin conditioning agent, and viscosity decreasing agents. Glycerine is virtually nontoxic, non-irritating, and odorless. It functions as a humectant, vehicle, and emollient. The U.S. Food and Drug Administration (FDA) includes glycerin on its list of direct food additives considered Generally Recognized As Safe (GRAS), and on its list of approved indirect food additives. Glycerin is also an FDA approved active ingredient in Over-the-Counter (OTC) skin protectant drug products, ear drying products and it an approved demulcent for the eyes. Glycerin in the formulation is required such as humectants and emollient agent, skin conditioning agent, skin protector, and viscosity decreasing agents.

Figure 6:
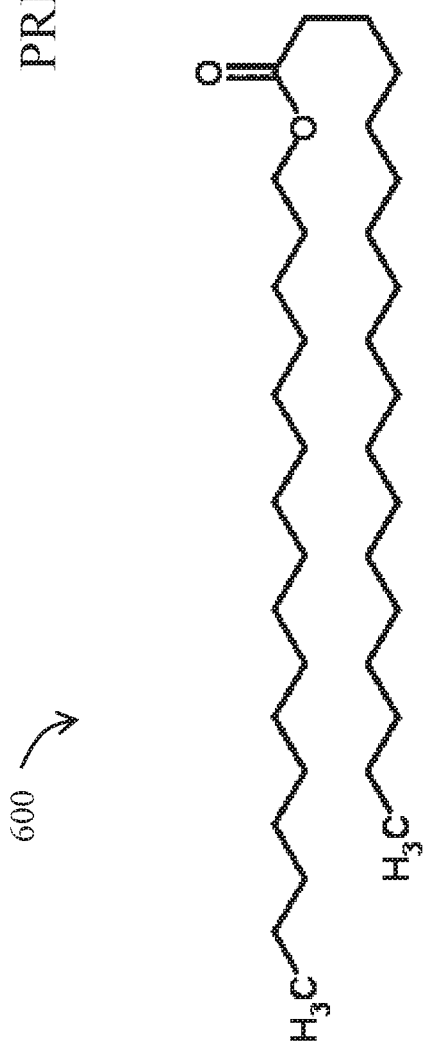
FIG. 6 is a perspective view of the molecular structure of cetearyl olivate.

Cetearyl olivate is an ester of the fatty acids from olive oil with ceatearyl alcohol, a naturally derived emulsifying wax, produced from a mixture of fatty alcohols. It is used in emollients, thickeners, and emulsion stabilizers. Cetearyl olivate is an emulsifier, which keeps ingredients from separating. It is a nonionic emulsifier that helps blend ingredients together in cosmetic solutions, usually ones with moisturizing properties. Cetearyl olivate has softening (for the skin and hair) qualities and gives products a smooth and luxurious feel. It's most often used in conjunction with sorbitan olivate and a common ingredient in personal care products such as facial moisturizers, sunscreens and lotions. Sorbitan olivate is a surfactant and emulsifier made from sorbitol and olive oil. Sorbitan olivate is an ester of the fatty acids from olive oil with sorbitol, a naturally derived moistener, from vegetable sugars. The molecular structure of cetearyl olivate is represented by the structure 600 shown in FIG. 6.

*Avena sativa* (oat) is a member of the Gramineae (grass) family. The kernel of *Avena sativa* can be ground into a flour. The solid components of an alcohol extract of ground and macerated *Avena sativa* seeds were reported to have a relative molecular mass of 1000 to 10,000 Da, as characterized by ultrafiltration. The average molecular weight of small peptides for a batch of hydrolyzed oats is 1365 Da. The high concentration of starch and β-glucan in colloidal oatmeal has a water-holding function; phenols have antioxidant and anti-inflammatory activity and act as ultraviolet absorbers. The cleansing activity of oat is from the saponins. As in all plants, there are large numbers of constituents that make up *Avena sativa* grains and other plant parts. The table below presents an overview of the constituent groups and subgroups of *Avena sativa*:

| Fractions | Subfractions | Main components | Plant part(s) |
| --- | --- | --- | --- |
| Oat starch | Carbohydrates | Amylose and amylopectin | Groats, flours, endosperm |
| | Lipids | Lysophospholipids and free fatty acids | Seed, bran, hull, endosperm |
| | Proteins | Peptides, amino acids, etc. | Groat, endosperm |
| | Inorganics | Calcium, magnesium, potassium | Hull, ash |

| Fractions | Subfractions | Main components | Plant part(s) |
| --- | --- | --- | --- |
| Non starch polysaccharides | Monosaccharides | Glucose, xylose, arabinose, galactose, mannose, uronic acid, fucose, rhamnose | Hull, bran |
| | Polysaccharides | B-glucan | Groats, endosperm |
| Phenolic compounds | Hydroxy benzoic acids and aldehydes | p-Hydroxybenzaldehyde, p-hydroxyphenyl acetic acid, p-hydroxybenzoic acid, salicylic acid, vanillin, vanillic acid, syringic acid, protocatechuic acid, cinnamic acid, p-coumaric acid, o-coumaric acid, caffeic acid, ferulic acid, sinapic acid | Whole oats, groats, hulls, flour, trolled oats, wholemeal, kernels |
| | Avenanthramides | Avenanthramide 2, Avenanthramide A, Avenanthramide C, Avenanthramide B, Avenanthramide E, Avenanthramide D, Z-Avenanthramide E | Leaves, groats, hulls, flour, whole oatmeal |
| | Phenolic glucosides | 2-Methoxyhydroquinone glucosides, p-hydroxybenzoic acid-4-O-b-d-glucoside, vanillic acid-4-O-b-d-glucoside, o-coumaric acid-4-O-b-d-glucoside, ferulic acid-4-O-b-d-glucoside | Oat seedlings, dehulled oats |
| Flavonoid | Aglycones | 2',4,4',6' -tetrahydroxy-3-methoxychalcone, apigenin, luteolin, tricin, leucodelphinidin, homo-eriodictyol | Oat kernel, whole plant |
| | Glycosyl flavones | Isovetexin, vitexin-rhamnoside, vicenin-2, isoswertisin-rhamnoside, isoorienlin, isoorientin-rhamnoside, luteolin glucosides, isoorieruin-glucoside, isoscoparin, tricinarabinoside, tricin-glucoside, tricin-arabinose, salcolin A, salcolin B | Leaves, stem, florets, whole plant, seedlings, kernel |
| Lignans | Aglycones | Pinoresinol, medioresinol, syringaresinol, lariciresinol, secoisolariciresinol, matairesinol | Oat flour, oat bran, kernel, Hull |
| Saponin | Glucosides | Avenacin A and B | Roots, kernels |
| Phenylpropanoid n-alkanol esters | Feruloyl and caffeoyl | Hexocosanols, octacosanol, hexacosadiols, hexacosanoic acid, Octacosanoic acid, and mixed esters | Oat flour, kernel, bran |
| Oat protein | Globulins | Globulin, glutelin, and albumin | Groat, kernel, hull, flakes |
| | Prolamins | Avenins | Seed, bran, groat |
| | Albumins | Limit dextrinase, Nuatigenin 3β-glucosyltransferase, Sterol 3β-glucosyltransferase More common: enzymes include lipase, lipoxygenase, and lipoperoxidase | Oat leaves, seeds, flakes, groat |
| | Peptides | Avenothionin alpha Avenothionin beta | |
| Oat lipids | Triacylglycerol | Oil contents 3-9%; Hybrid varieties of oats have triacylglycerol content as high as 18% | Seeds, bran, endosperm |
| | Free fatty acids | Fatty acids | Oat bran, oat oil |
| | Phospholipids and Glycolipids | | Seed, bran |
| | Oxylipins | | Oat seed, leaves, oat oil |
| Minerals | | Potassium, phosphorus, magnesium, calcium, sodium, iron, zinc, manganese, copper | Ash, hull, bran |
| Vitamins | | Vitamin E (tocols), niacin, pantothenic acid, thiamin, vitamin B6, riboflavin, folic acid, biotin, choline | Bran |

Figure 7:
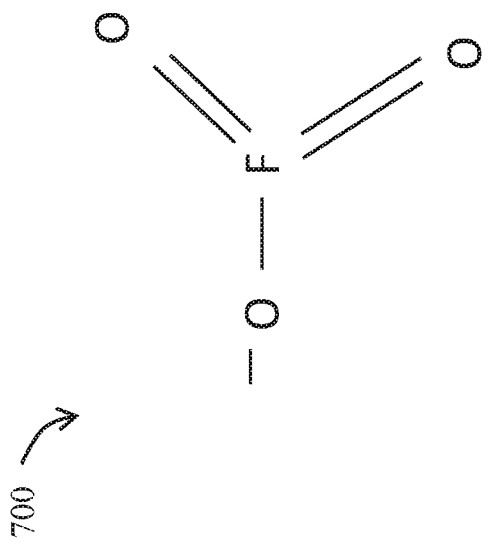
FIG. 7 is a perspective view of the molecular structure of *Avena sativa* (oat) kernel flour.

*Avena sativa* (oat), marigold, zinc PCA, tocopherol acetate and sodium ascorbyl phosphate serve as the base for the lotion 100. *Avena sativa* (oat) has anti-inflammatory and anti-itch properties that were approved in 2003 by the FDA as a skin protectant. Studies have shown that avenanthramides (colloidal oatmeal) can reduce the production of pro-inflammatory cytokines such as 1L-6, 1L-8, MCP1 by inhibiting NF-KB activation which is responsible to activate the genes of inflammatory response. The aforementioned qualities lead to a decrease of inflammation by inhibiting cytokine release. Also, colloidal oatmeal reduces neurogenic inflammation which is inflammation triggered by the nervous system causing vasodilation, edema and hypersensitivity. The anti-itch reduction caused by colloidal oatmeal is comparable to hydrocortisone. The molecular structure of *Avena sativa* is represented by the structure 700 shown in FIG. 7.

Avenanthramides (anthranilic acid amides) are a group of phenolic alkaloids found mainly in oats (*Avena sativa*). A number of studies demonstrate that these natural products have anti-inflammatory, antioxidant, anti-itch, anti-irritant, and antiatherogenic activities.

Figure 8:
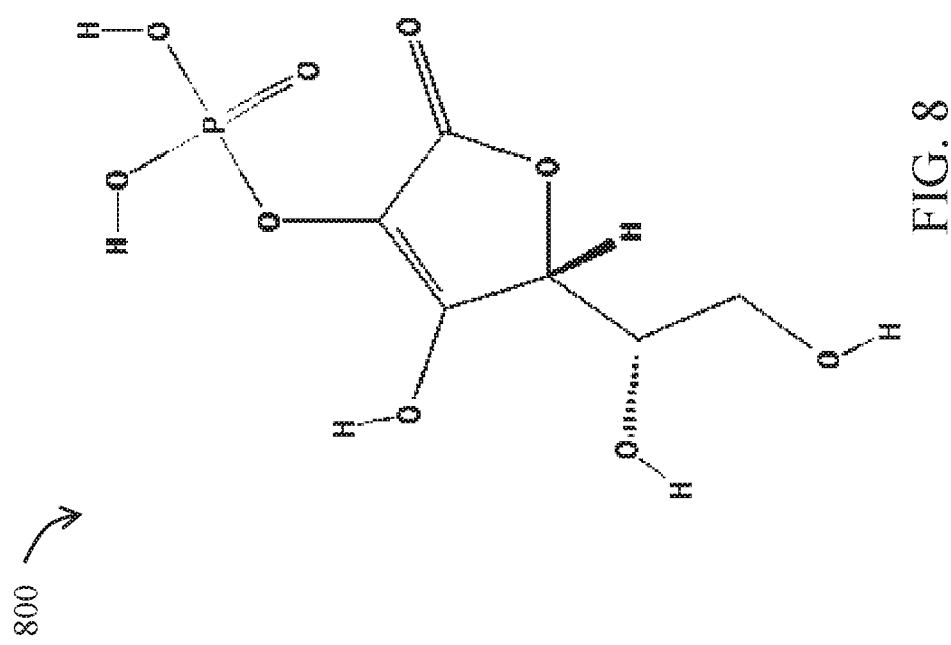
FIG. 8 is a perspective view of the molecular structure of sodium ascorbyl phosphate.

Sodium ascorbyl phosphate ($C_6H_6Na_3O_9P$), or SAP, is a stable, water-soluble form of vitamin C that functions as an antioxidant. SAP cleaves enzymatecaly to skin and releases active vitamin C. It should be noted that vitamin C is also known as ascorbic acid, which is a vitamin found in food and used as a dietary supplement. SAP woks as an effective antioxidant of skin, protects skin damage caused by free radicals, and promotes collagen formation. To protect fibroblasts from the damaging effects of physical and chemical external factors, a natural compound such ascorbic acid is often used. It participates in the main phospholipid protection mechanisms in the cell including glutathione (GSH) and vitamin E. Ascorbic acid applied to the skin provides significant protection against erythema and sunburn cell formation. Recent studies of ascorbic acid show photoprotective potential and normalizea MMP-1 mRNA and mitochondrial membrane polarization in UVA-irradiated human skin fibroblasts. Moreover, ascorbic acid in fibroblasts is essential for collagen biosynthesis as a cofactor for prolyl and lysyl hydroxylase and as a stimulus for collagen gene expression. As an effective water soluble anti-oxidant which is stable in cosmetic formulation, ascorbic acid is the ideal complement to vitamin E acetate, which is the common oil-soluble equivalent. The oil-soluble vitamin E acetate together with the water-soluble sodium ascorbyl phosphate are the ideal anti-oxidant system in all skin-care formulations which are used against the daily environmental stresses working against the skin. Studies show that vitamin E acetate and sodium ascorbyl phosphate used together have a synergistic effect for the inhibition of oxidation. The effect is much higher than with the single compounds alone. Due to their different solubilities, SAP protects the aqueous cytosol part of the system, while vitamin E acetate is incorporated into the oil-soluble cell-membranes. The synergistic effect of SAP and vitamin E acetate is therefore due to the fact that only a combination of a water-soluble with a fat-soluble antioxidant offers integral protection. The molecular structure of sodium ascorbyl phosphate is represented by the structure 800 shown in FIG. 8.

Figure 9:
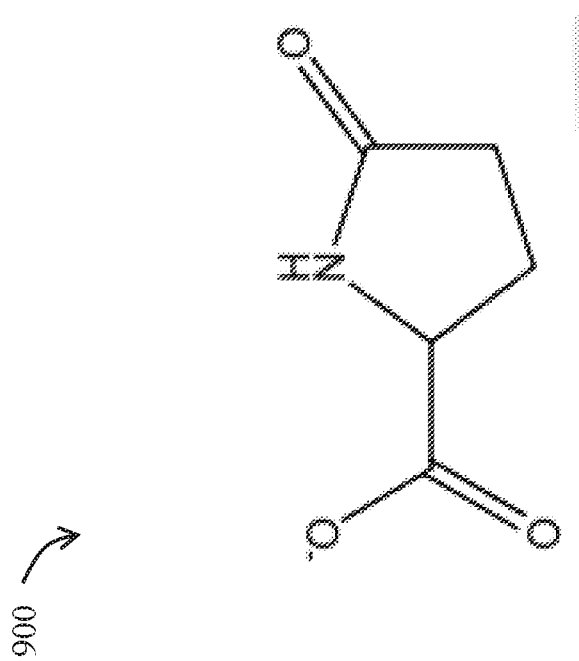
FIG. 9 is a perspective view of the molecular structure of Zinc PCA.

Zinc PCA is the zinc salt of Pyrrolidone Carboxylic Acid (PCA). It is a skin conditioning agent used in personal care products because of its astringent and antimicrobial properties. It is used in a wide range of personal care products including gels, creams, lotions and foundations. Zinc PCA is also used in facial-care and anti-acne products as well as in special shampoos. Zinc PCA has antimicrobial and astringent properties and suppresses UVA-induced activation of activato protein 1 (AP-1), while reducing metrix metalloproteinase-1 production in cells, which is thought to be involved in collagen degradation in skin exposed to sun light. Zinc PCA treated cells increase the expression of the ascorbic acid transporter of mRNA, SVCT2 (sodium dependent vitamin C transporter 2), but not SVCT1 which results in enhanced production of type 1 collagen. Zinc plays an important role in maintaining proper reproductive function, immune status, and wound repair via regulation of DNA and RNA polymerases, thymidine kinase, and ribonuclease. It also possesses antioxidant properties and has been found useful in preventing UV-induced damage and reducing the incidence of malignancies. Zinc, alone or as an adjuvant, has been found useful in many dermatological infections owing to its modulating actions on macrophage and neutrophil functions, natural killer cell/phagocytic activity, and various inflammatory cytokines. The molecular structure of Zinc PCA is represented by the structure 900 shown in FIG. 9.

Figure 4:
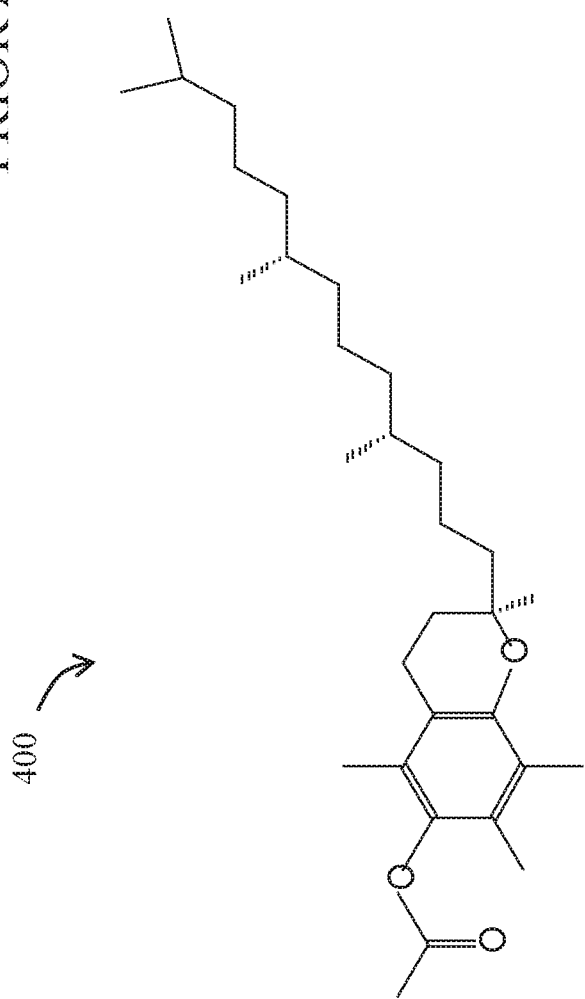
FIG. 4 is a perspective view of the molecular structure of tocopherol acetate.

Tocopherol acetate, meaning tocopheryl acetate, vitamin E acetate, DL-alpha-tocopheryl acetate, ephynal, syntopherol acetate, and rovimix E 50SD is a collective name for a group of closely related lipids that contain substitutions on the 2H-1-benzopyran-6-ol nucleus and a long hydrocarbon chain of isoprenoid units may function in the formulation as an antioxidant and skin conditioning agent, as represented by the molecular structure 400 shown in FIG. 4.

Tocopherol acetate is a powerful antioxidant that helps to protect cell membranes, making it a great ingredient as a dry skin protector agent. The CIR Expert Panel evaluated the scientific data and concluded that tocopherol and the related ingredients were safe as used in cosmetics and personal care products. Tocopherol acetate in the formulation is required such as an antioxidant and skin conditioning agent.

d-Alpha-Tocopherol is a naturally-occurring form of vitamin E, a fat-soluble vitamin with potent antioxidant properties. Considered essential for the stabilization of biological membranes (especially those with high amounts of polyunsaturated fatty acids), d-alpha-Tocopherol is a potent peroxyl radical scavenger and inhibits noncompetitively cyclooxygenase activity in many tissues, resulting in a decrease in prostaglandin production. Vitamin E also inhibits angiogenesis and tumor dormancy through suppressing vascular endothelial growth factor (VEGF) gene transcription. Vitamin E (alpha tocopherol) is also believed to be important in protecting cells from oxidative stress, regulating immune function, maintaining endothelial cell integrity and balancing normal coagulation. By strengthening the skin barrier function and reducing transepidermal water loss, it enhances moisturization of skin and protects the skin barrier's lipid balance.

*Calendula officinalis*, common marigold, is a plant in the genus *Calendula* of the family Asteraceae. The petals and pollen of *Calendula officinalis* contain triterpenoid esters and the carotenoids flavoxanthin and auroxanthin (antioxidants and the source of the yellow-orange coloration). The leaves and stems contain other carotenoids, mostly lutein (80%), zeaxanthin (5%), and beta-carotene. The flowers of *Calendula officinalis* contain flavonol glycosides, triterpene oligoglycosides, oleanane-type triterpene glycosides, saponins, and a sesquiterpene glucoside. Extracts are also widely used by cosmetics, due to presence of compounds such as saponins, resins, and essential oils. Plant pharmacological studies have suggested that *Calendula* extracts may have anti-viral, anti-genotoxic, and anti-inflammatory properties in vitro. In an in vitro assay, the methanol extract of *Calendula officinalis* exhibited antibacterial activity and both the methanol and the ethanol extracts showed antifungal activities.

Figure 10:
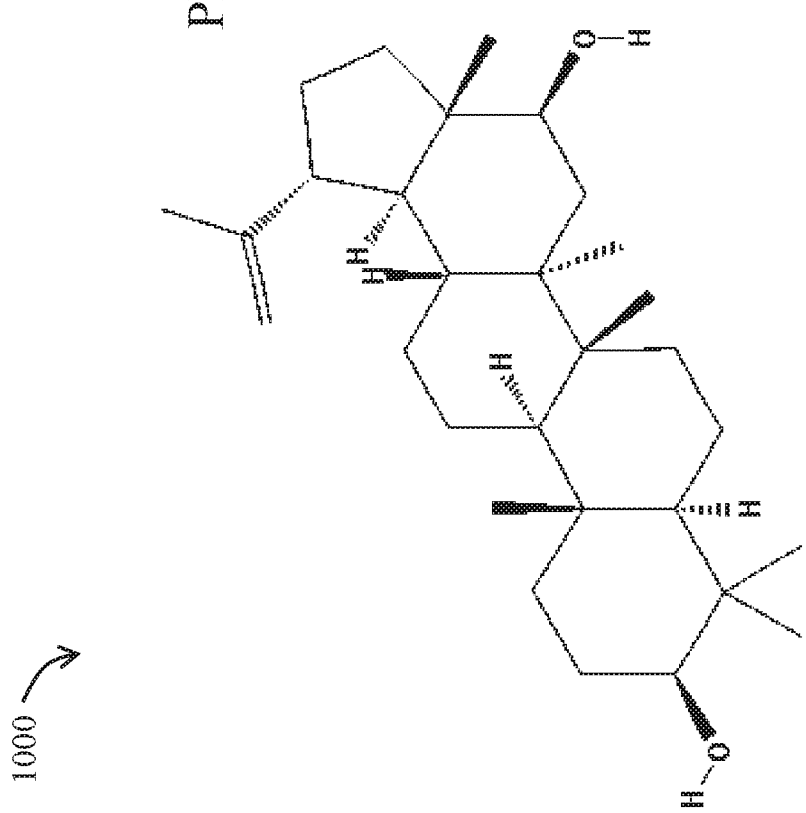
FIG. 10 is a perspective view of the molecular structure of calenduladiol, which is a terpinoid of *Calendula officinalis* (marigold) flower extract.

*Calendula officinalis* has been used for medicinal purposes since at least the 12$^{th}$ century, primarily as a topical application to boost the healing rate of wounds and prevent infection. *Calendula officinalis* contains high amounts of flavonoids, which are thought to increase the rate of neovascularization and deposit hyaluronan, the principal component of the extracellular matrix in cells. Hyaluronan contributes to cell proliferation and migration as well as the formation, alignment and migration of capillaries, which may explain why *Calendula* speeds healing. The antifungal properties of *Calendula* could make it useful as an herbal remedy for fungal infections like thrush, athlete's foot, and ringworm. *Calendula officinalis* extract is beneficial for the treatment of damaged skin. It has been used to stimulate granulation, enhances formation of cell tissue, accelerates wound healing and has an anti-inflammatory and pain killing effect. It is used to cure decubitus, burns, eczema, bee stings, swelling and inflammation of varicose veins and hemorrhoids. Plant pharmacological studies have suggested that *Calendula officinalis* extracts may have antiviral, anti-genotoxic, and anti-inflammatory properties in vitro. The molecular structure of calenduladiol, which is a terpinoid of *Calendula officinalis* (marigold) flower extract is represented by the structure 1000 shown in FIG. 10.

Figure 11:
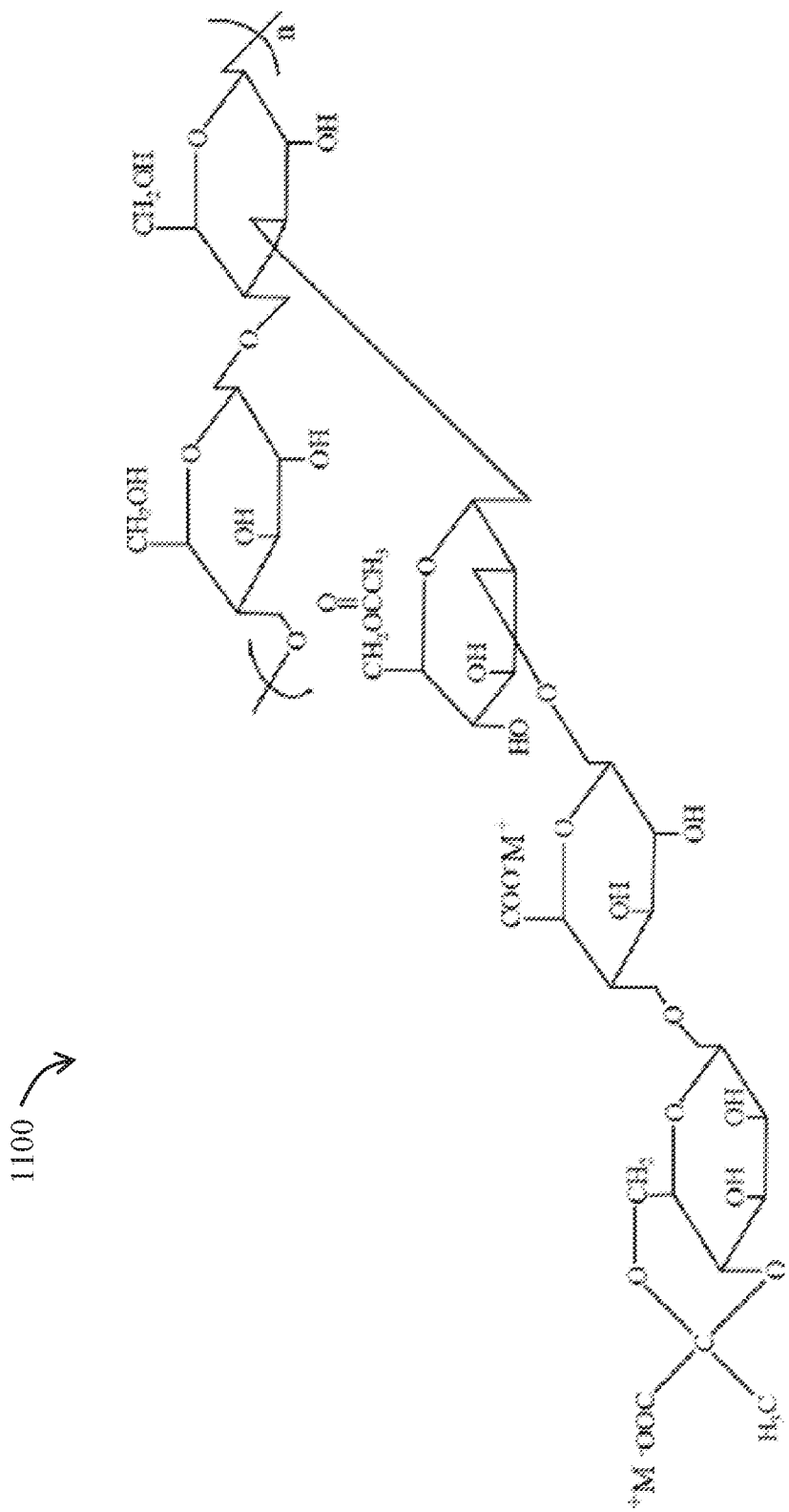
FIG. 11 is a perspective view of the molecular structure of xantham gum.

Xanthan gum is a polysaccharide produced by the fermentation of glucose, sucrose, or lactose. Xanthan gum has many industrial uses, including as a common food additive. It is an effective thickening agent and stabilizer to prevent ingredients from separating. The molecular structure of xantham gum is represented by the structure 1100 shown in FIG. 11.

Figure 12:
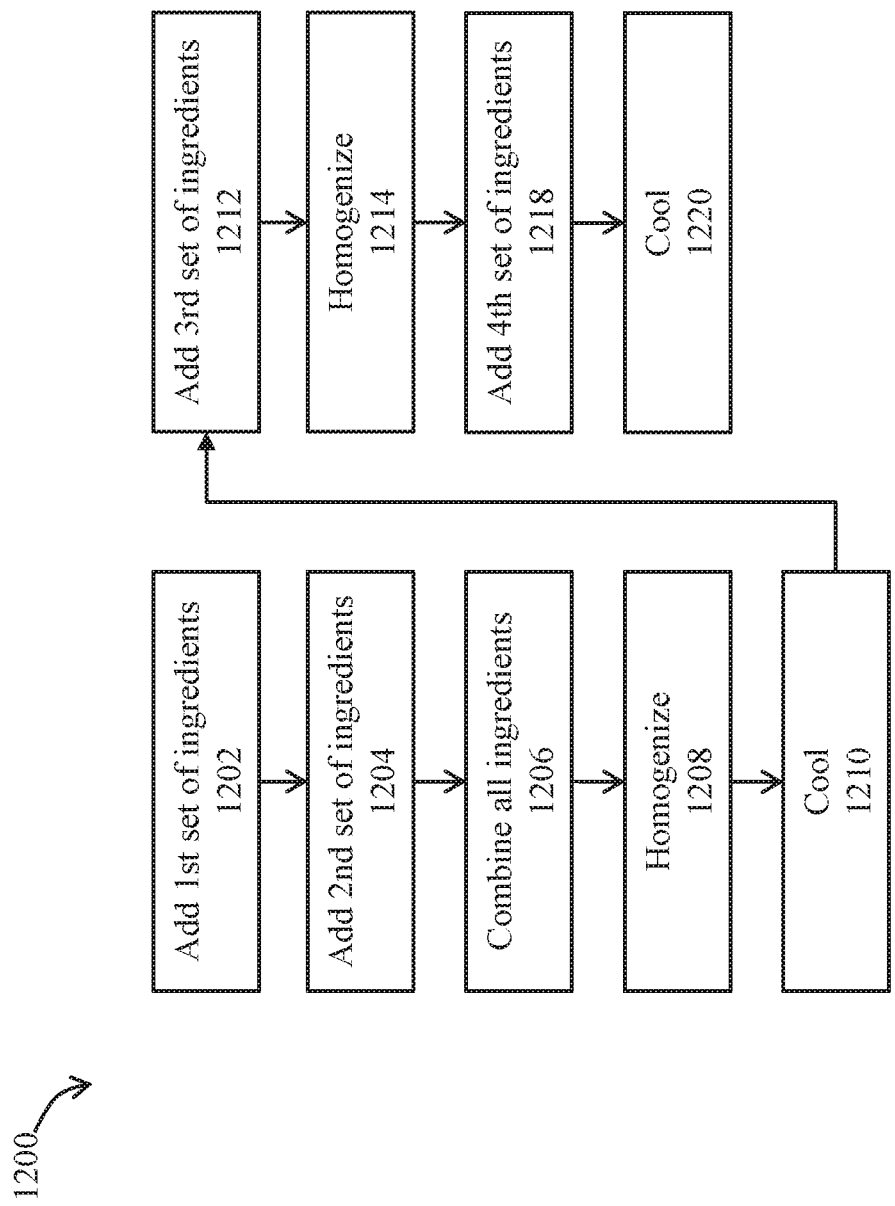
FIG. 12 is a flow chart illustrating the steps of preparing the disclosed oat and marigold-based composition with anti-inflammatory and wound healing action.

The lotion for topical application with broad spectrum anti-inflammatory and wound healing action is provided by a method of preparation 1200 outlined in FIG. 12. In step 1202, the following ingredients are added to a first vessel: deionized water, glycerin, *Avena sativa* kernel flour, zinc PCA, and xantham gum in amounts depending on batch size and equipment configuration. The ingredients in the first vessel are also heated to a temperature depending on batch size and equipment configuration. In one embodiment, the ingredients in the first vessel are heated to about 80 degrees Celsius and are added in the following amounts: about 25.0 to 80.0 grams of deionized water, about 0.5 to 6.0 grams of glycerin, about 0.5 to 2.0 grams of *Avena sativa* kernel flour, about 0.10 to 5.0 grams of zinc PCA, and about 0.10 to 5.0 grams of xantham gum.

In step 1204, the following ingredients are added to a second vessel: caprylic/capric triglyceride, cetyl alcohol, cetearyl olivate and sorbitan olivate, and *Calendula officinalis* flower extract. The ingredients in the second vessel are also heated to a temperature depending on batch size and equipment configuration. In one embodiment, the ingredients in the second vessel are heated to about 80 degrees Celsius and are added in the following amounts: about 1.0 to 12.0 grams of caprylic/capric triglyceride, about 0.5 to 10.0 grams of cetyl alcohol, about 0.5 to 10.0 grams of cetearyl olivate and sorbitan olivate, and about 0.05 to 5.0 grams of *Calendula officinalis* flower extract.

In step 1206, the ingredients of the first vessel are added to the ingredients in the second vessel and mixed until a mixture is created, such as mixing for about 10 minutes, depending on batch size and equipment configuration.

In step 1208, the mixture in the second vessel is mixed until homogenized, such as after mixing for about 3 minutes, depending on batch size and equipment configuration. The mixing may be accomplished via stirring or other types of movement.

In step 1210, the mixture is allowed to cool, such as to about 40 degrees Celsius, depending on batch size and equipment configuration.

In step 1212, the following ingredients are added to the mixture in the second vessel: deionized water, sodium ascorbyl phosphate, and tocopheryl acetate. In one embodiment, the ingredients are added in the following amounts: about 25.0 to 80.0 grams of deionized water, about 0.05 to 2.0 grams of sodium ascorbyl phosphate, and about 0.05 to 5.0 grams of tocopheryl acetate In step 1214, the mixture is mixed until homogenized, such as after mixing for about 2 minutes, depending on batch size and equipment configuration.

In step 1218, the following ingredient is added to the mixture in the second vessel: a preservative mixture solution, such as at least 0.05 grams of said solution, depending on batch size and equipment configuration. In step 1220, the mixture in the second vessel is allowed to cool, such as to about 25 to 30 degrees Celsius, depending on batch size and equipment configuration.

The current composition 100 was formulated in a cream or lotion emulsion but it is not limited to said type of base. The composition 100 may be formulated in a gel, liquid, mousse, oil, spray, etc.

Preliminary experimental results in several case studies showed positive results in treating several individual skin conditions. The time exhibited for the healing process for various skin conditions was dramatically reduced (within 10-14 days) when using the composition 100. In all cases, the affected skin condition was completely healed. The reduced healing time and the effectiveness of the composition 100 as a treatment, makes it possible to eliminate or tremendously reduce the potential for scarring and reconstituting an even skin tone.

In said experimental studies, it was noted that one burn victim presented a 2nd degree burn which healed with virtually no scars and with even skin tone when using the composition 100. On several occasions, when the composition 100 was used on the skin condition of a child patient, the clinic had to call the parent to ask about the child's skin condition (eczema, atopic dermatitis), only to find out that the parent forgot to bring the patient back for the follow up just because the child's skin was completely healed after 1 week of treatment with the composition 100, i.e., a positive outcome. This invention shows positive results with preliminary screening on a limited population of patients. The composition 100 proved to be effective for efficient healing that is at the least equal and potentially more efficient than the classic steroidal treatments and without any anticipated or known side effects.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

We claim:

1. A lotion for topical application to skin, comprising of:
   about 0.5 to 2.0 percent by weight of *Avena sativa* kernel flour;
   about 0.05 to 2.0 percent by weight of sodium ascorbyl phosphate;
   about 0.10 to 5.0 percent by weight of zinc PCA;
   about 0.05 to 5.0 percent by weight of tocopheryl acetate; and
   about 0.05 to 5.0 percent by weight of *Calendula officinalis* flower extract.

* * * * *